United States Patent [19]

Miyashita

[11] Patent Number: 5,288,592
[45] Date of Patent: Feb. 22, 1994

[54] TRANSITION METAL-SPIROBENZOPYRAN COMPLEX, A PRODUCTION PROCESS THEREFOR AND A PHOTOCHROMIC MATERIAL COMPRISING THE COMPLEX

[75] Inventor: Akira Miyashita, Ageo, Japan

[73] Assignee: Otsuka Kagaku Kabushiki Kaisha, Osaka, Japan

[21] Appl. No.: 938,044

[22] PCT Filed: Mar. 12, 1992

[86] PCT No.: PCT/JP92/00295
§ 371 Date: Nov. 12, 1992
§ 102(e) Date: Nov. 12, 1992

[87] PCT Pub. No.: WO92/16538
PCT Pub. Date: Oct. 1, 1992

[30] Foreign Application Priority Data

Mar. 13, 1991 [JP] Japan .................... 3-047202

[51] Int. Cl.$^5$ .................. G03C 1/735; C07D 209/96
[52] U.S. Cl. .................... 430/345; 430/962; 252/586; 548/402; 548/409
[58] Field of Search .............. 430/345, 962; 252/586; 548/409, 402, 401

[56] References Cited

U.S. PATENT DOCUMENTS

| | | | |
|---|---|---|---|
| 3,299,079 | 1/1967 | Taylor | 548/409 |
| 3,510,308 | 5/1970 | Foris et al. | 252/586 |
| 3,923,524 | 12/1975 | Haase | 430/83 |
| 3,950,356 | 4/1976 | Hinnen | 548/409 |
| 4,725,527 | 2/1988 | Robillard | 430/339 |
| 5,045,420 | 9/1991 | Hosono et al. | 430/45 |

FOREIGN PATENT DOCUMENTS

| | | |
|---|---|---|
| 59-202270 | 11/1984 | Japan . |
| 60-054388 | 3/1985 | Japan . |
| 63-267783 | 11/1988 | Japan . |
| 2-069739 | 3/1990 | Japan .................. 252/586 |
| 2-212585 | 8/1990 | Japan .................. 252/586 |

OTHER PUBLICATIONS

"New Experimental Chemical Lecture (No. 12) Organic Metal Chemistry", Japan Chem. Soc., (Mar. 1976).
J. Amer. Chem. Soc. 87, 4020 (1965), Phillips et al.
J. Chem. Soc., Chem. Commun., (1989), Tamaki et al.
Proceedings of the 58th Spring Meeting of the Chemical Society of Japan 1874 (1989), Oda et al.
Proceedings of the 59th Spring Meeting of the Chemical Society of Japan 1883 (1990), Tamaki et al.
Chemical Society of Japan (Lectures on New Experimental Chemistry) Organo Metallic Chemistry p. 114 (1979).

*Primary Examiner*—Charles L. Bowers, Jr.
*Assistant Examiner*—John A. McPherson
*Attorney, Agent, or Firm*—Armstrong, Westerman, Hattori, McLeland & Naughton

[57] ABSTRACT

The object of the invention is to provide a novel compound exhibiting stable photochromism.

The invention is directed to a transition metal-spirobenzothiopyran complex of the general formula

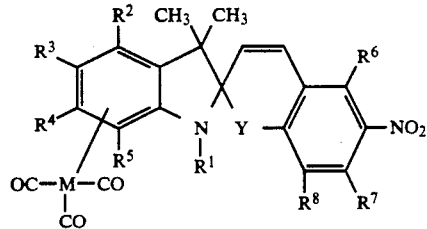

wherein $R^1$ for example be $C_{1-20}$ alkyl; $R^2$, $R^3$, $R^4$, $R^5$, $R^6$, $R^7$ and $R^8$ independently may mean hydrogen; Y means O or S; M may for example be Cr, and a process for producing the complex.

3 Claims, 2 Drawing Sheets

TRANSITION METAL-SPIROBENZOPYRAN COMPLEX, A PRODUCTION PROCESS THEREFOR AND A PHOTOCHROMIC MATERIAL COMPRISING THE COMPLEX

TECHNICAL FIELD

The present invention relates to a transition metal-spirobenzopyran complex, a process for producing the complex, and a photochromic material comprising the complex.

BACKGROUND ART

The organic compounds undergoing a reversible change of color on exposure to photic or thermal energy which are typical and best known are spiropyran derivatives and G. H. Brown: Photochromism (John Wiley & Sons, Inc., 1971), for one, can be consulted for a specific listing of such derivatives and their physical properties.

However, when an attempt is made to exploit the hitherto-known spiropyran derivatives commercially in recording materials, they are found to have serious disadvantages. Thus, because the meta-stable species (ring opened isomers) are lacking in thermal stability in solutions as well as in polymeric binders, they tend to promptly revert to the ground state or fade out so that the chromic response at a necessary level cannot be sustained for a sufficient duration.

It is an object of the present invention to provide a compound free from the above-mentioned disadvantages of the prior art spiropyran derivatives.

It is a further object of the present invention to provide a compound exhibiting stable photochromism.

DISCLOSURE OF THE INVENTION

The inventor of the present invention explored in earnest for a solution to the above problems and found that a certain transition metal-spirobenzopyran complex is able to solve the above problems. The present invention has been developed on the basis of the above finding. The present invention accordingly has achieved a successful fixation of the colored form of spiropyrans which have been acknowledged to be thermally labile.

The transition metal-spirobenzopyran complex of the present invention is a novel compound which has not been described in the literature. It is a transition metal-spirobenzopyran complex of the following general formula.

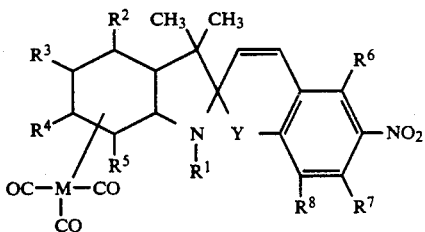
(1)

wherein $R^1$ means an alkyl group of 1 to 20 carbon atoms or an aralkyl group. $R^2$, $R^3$, $R^4$ and $R^5$ may be the same or different and each means a hydrogen atom, an alkyl group of 1 to 6 carbon atoms, an aryl group, an aralkyl group, an alkoxy group of 1 to 5 carbon atoms, a halogen atom, a cyano group or a nitro group. $R^6$ and $R^7$ may be the same or different and each means a hydrogen atom, an alkyl group of 1 to 6 carbon atoms, an aryl group, an aralkyl group, a halogen atom, a cyano group or a nitro group. $R^8$ means a hydrogen atom, an alkyl group of 1 to 6 carbon atoms, an alkoxy group of 1 to 5 carbon atoms, a chloromethyl group, a methacryloxymethyl group or a vinyl group. Y means an oxygen atom or a sulfur atom. M means a chromium atom, a molybdenum atom or a tungsten atom.

The addition of metal salts to photochromic compounds, such as spiropyrans and spironaphthoxazines, in an attempt to stabilize less stable colored form is reported, inter alia, in J. Amer. Chem. Soc. 87, 4020 (1965), J. Chem. Soc. Chem. Commun., 1477 (1989), the Proceedings of the 58th Spring Meeting of The Chemical Society of Japan, 1874 (1989) and the Proceedings of the 59th Spring Meeting of the same Society, 1983 (1990). According to Akio Yamamoto: Yukikinzoku Kagaku—Kisoto-Ooyo [Organometallic Chemistry—Fundamentals and Applications] (Syokabo, 1982), the term "organometallic compound" means a compound in which at least one metal element or semi-metal (metalloid) element is bound to the carbon atom of an organic group. However, the prior art compounds represented by the species referred to above invariably involve bonding between a carbon compound and a metal atom through a hetero-atom (oxygen, nitrogen or the like) and these species are, by convention, not called organometallic compounds.

Thus, the complex of the present invention is an organometallic compound in the true sense of the term in that there exist six metal-carbon bonds between the indoline moiety of an indolinospirobenzopyran and a transition metal of the VIA group, and is a quite novel transition metal-spirobenzopyran complex.

The transition metal-spirobenzopyran complex of general formula (I) according to the present invention can be produced by reacting an organometal complex of the general formula

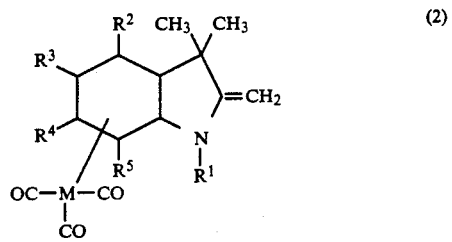
(2)

wherein $R^1$, $R^2$, $R^3$, $R^4$, $R^5$ and M are as defined hereinbefore with a 5-nitro(thio)salicylaldehyde derivative of the general formula

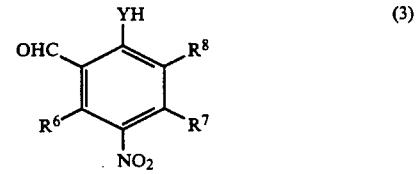
(3)

wherein $R^6$, $R^7$, $R^8$ and Y are as defined hereinbefore.

The compound of general formula (2) which is used as a starting compound in the present invention can be synthesized by reacting a 3,3-dimethyl-2-methyleneindoline derivative of the general formula

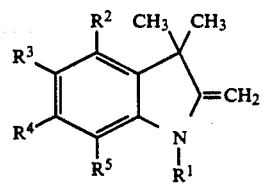

(4)

wherein $R^1$, $R^2$, $R^3$, $R^4$ and $R^5$ are as defined hereinbefore with hexacarbonyl chromium, hexacarbonyl molybdenum or hexacarbonyl tungsten in the known manner as described inter alia in the Chemical Society of Japan (ed.): Shin Jikken Kagaku Koza (Lectures on New Experimental Chemistry), vol. 12 and Yuki Kinzoku Kagaku (Organometallic Chemistry), page 114 (Maruzen, 1979).

Furthermore, the above compound of general formula (4) can be easily produced by treating a 2,3,3-trimethylindolenium iodide of the general formula

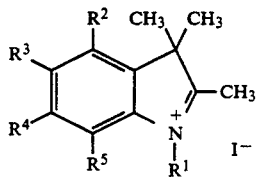

(5)

wherein $R^1$, $R^2$, $R^3$, $R^4$ and $R^5$ are as defined hereinbefore with a base such as an alkali hydroxide. Regarding the above 2,3,3-trimethylindolenine derivatives, some species are the known compounds described in Helv. Chim. Acta, 23, 2471 (1940), Japanese Patent Publication No. 58654/1983, Japanese Kokai Patent Publication No. 232461/1987, Japanese Patent Publication No. 21780/1987 and Japanese Kokai Patent Publication No. 267783/1988, for instance, while others are compounds which can be easily prepared in accordance with the processes described in the above literature.

Meanwhile, the compound of general formula (3) wherein Y is S can be produced by reacting a 5-nitrosalicylaldehyde derivative of general formula (6)

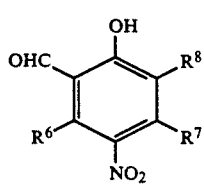

(6)

wherein $R^6$, $R^7$ and $R^8$ are as defined hereinbefore which is readily available, with an N,N-dimethylthiocarbamoyl chloride, for example in the same manner as described in Japanese Kokai Patent Publication No. 54388/1985, to give a 2-O-(N,N-dimethylthiocarbamoyl)benzaldehyde of the general formula

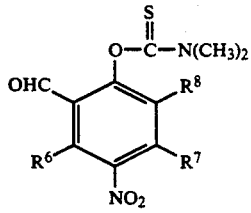

(7)

wherein $R^6$, $R^7$ and $R^8$ are as defined hereinbefore, then heating the same to isomerize to give a 2-S-(N,N-dimethylthiocarbamoyl)benzaldehyie derivative of the general formula (8)

wherein $R^6$, $R^7$ and $R^8$ are as defined hereinbefore, and further subjecting this derivative to alkali hydrolysis.

The transition metal-spirobenzopyran complex of general formula (1) according to the present invention can be produced by reacting the above organometallic complex of general formula (2) with the 5-nitro(thio)-salicylaldehyde derivative of general formula (3) in an organic solvent in the absence of air.

The organic solvent which can be used in the production of the transition metal-spirobenzopyran complex of general formula (1) includes a broad range of solvents which are inert under the conditions of the reaction, for example lower alcohols such as methanol, ethanol, propanol, isopropyl alcohol, n-butanol, isobutyl alcohol, t-butyl alcohol, etc.; ethers such as diethyl ether, dimethoxyethane, tetrahydrofuran, dioxane, etc.; amides such as formamide, dimethylformamide, acetamide, dimethylacetamide, etc.; ketones such as acetone, methyl ethyl ketone, methyl isobutyl ketone, etc.; lower carboxylic acid esters such as methyl formate, ethyl formate, methyl acetate, ethyl acetate, butyl acetate, etc.; and aromatic hydrocarbons such as benzene, toluene, xylene and so on. The amount of the solvent may be such that the concentration of the compound of general formula (2) will be in the range of 0.001 mole/l to saturation concentration. While it depends on the solvent species used, the reaction temperature may range from 0° C. to the boiling point of the solvent used and is preferably in the range of room temperature to 100° C. The reaction time is generally 1 to 150 hours.

The resulting complex of general formula (1) generally separates out as crystals from the reaction mixture. Therefore, they can be isolated by the conventional procedure such as filtration and centrifugation. If the complex does not separate out as crystals, it can be isolated by concentrating the reaction mixture.

The transition metal-spirobenzopyran complex of general formula (1), which is produced by the above production process, exhibits stable photochromism. The colored species obtainable by dissolving the complex of general formula (1) in an appropriate solvent and irradiating the resulting solution with ultraviolet light is particularly stable against heat and whereas the colored species of the free spirobenzopyran derivative not ligated to a transition metal loses its color rapidly at room temperature, the colored species of the compound of the invention is characterized by achieving thermally stable fixation of colored state following some initial fading.

The application of the complex of the invention as a photochromic material is now described.

The photochromic material of the invention can be manufactured by dissolving the complex of the invention together with a polymer substance in a solvent, e.g. an ether such as diethyl ether, dibutyl ether, tetrahydrofuran, etc., a hydrocarbon such as benzene, toluene, xylene, etc., dimethylformamide, dimethyl sulfoxide or the like, and casting it into a sheet form or coating a support with it and drying the coat. The polymer substance mentioned above can be selected from a broad class of known substances only if they are highly compatible with the complex of the invention and conductive to formation of a uniform film. Thus, for example, polymethyl methacrylate, polyvinyl acetate, polyvinyl butyral, polystyrene, polyvinyl chloride, polyvinylidene chloride, polyethylene, polypropylene polyurethane, etc., may be mentioned. The support material may be any of polyethylene terephthalate, polycarbonate, polyacrylate, glass, metal and other pertinent materials.

The photochromic material of the present invention can be chromically excited by irradiation with ultraviolet light and brought back into its unexcited state by irradiation with visible light ($\geq 500$ nm) and is capable of undergoing this cycle repeatedly without fatigue. The material according to the invention having such characteristics finds application in a variety of fields such as recording materials, laser photosensitive materials, optical filters, displays, decorations and so on.

BEST MODE FOR CARRYING OUT THE INVENTION

Figure 1:
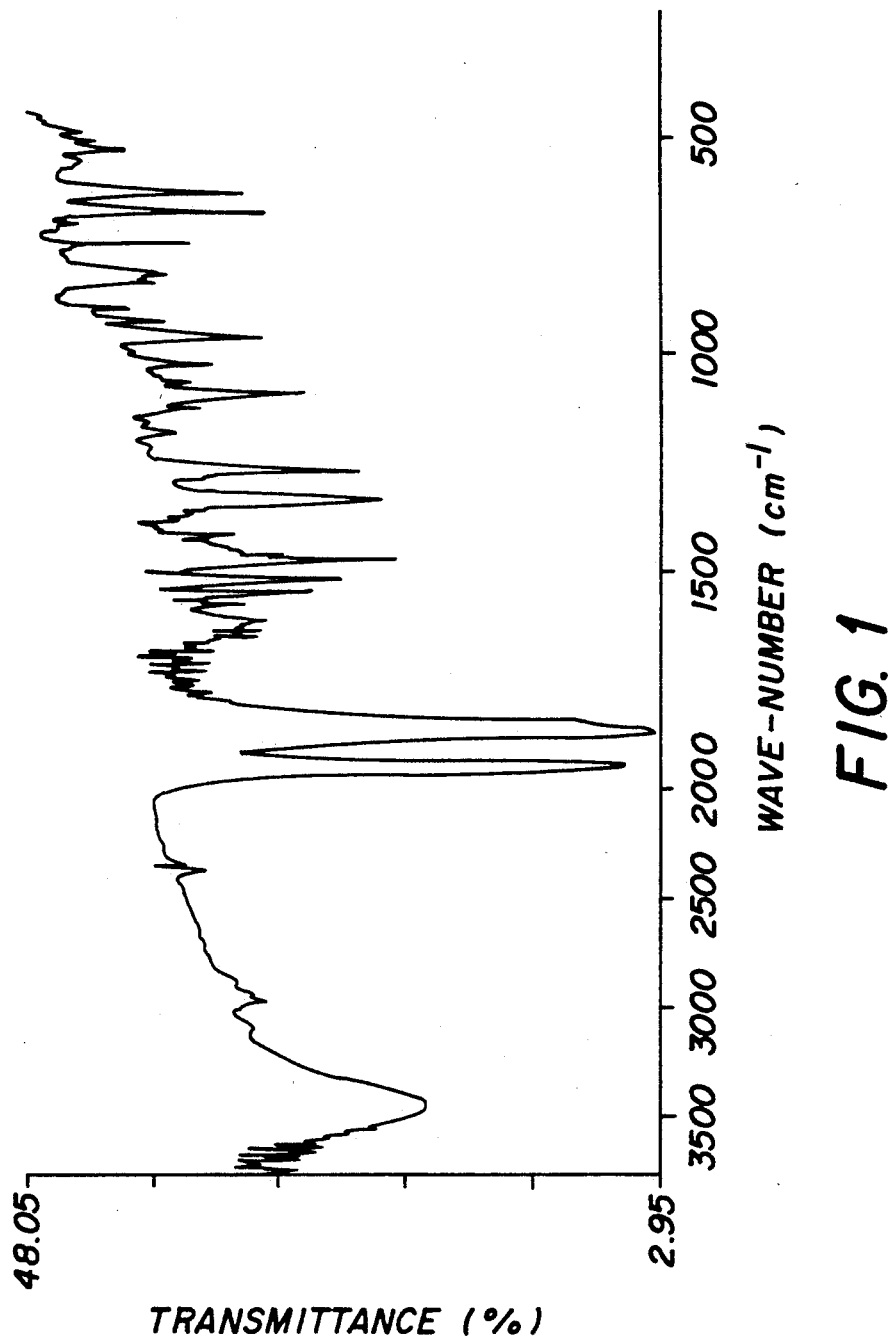
FIG. 1 is an IR spectrum of the complex of the invention as obtained in Example 4.

The following examples are intended to describe the present invention in further detail.

Example 1

2,3,3-Trimethylindolenine (3.26 g, 20.5 mmol) was added to 7 ml of chloroform followed by addition of methyl iodide (3.20 g, 22.5 mmol) and the mixture was heated in an ampule at 80° C. for 17 hours. The reaction mixture changed in due course from a red solution to a red suspension. After completion of the reaction, this suspension was suction-filtered to recover a red precipitate which was then washed with chloroform and diethyl ether under ice-cooling. The pink powder thus obtained was found to be 1,2,3,3,-tetramethylindolenium iodide.

Yield 5.7 g, 94% $^1$H-NMR (D$_2$O) $\delta$ppm
1.65 (s, 6H, 3-CH$_3$), 2.87 (s, 3H, 2-CH$_3$), 4.10 (s, 3H, N-CH$_3$), 7.5–7.8 (m, 4H, aromatic H)

EXAMPLE 2

In an aqueous solution of potassium hydroxide (0.7 mol/l, 107 mmol) was suspended 1,2,3,3-tetramethylindolenium iodide (1.5133 g, 5.03 mmol) and the suspension was stirred at room temperature for 1 hour, whereby a yellow oil was produced in the reaction system. This oil was extracted with diethyl ether and the extract was washed with saturated aqueous sodium chloride solution until a neutral aqueous wash was obtained. Then, the extract was dried by addition of anhydrous sodium sulfate and the ether was distilled off to give 1,3,3-trimethyl-2-methyleneindoline as a red liquid.

Yield 807.2 mg, 93%
$^1$H-NMR (CDCl$_3$): $\delta$ppm
1.3 (s, 6H, 3-CH$_3$), 3.1 (s, 3H, N-CH$_3$), 4.0 (s, 2H, =CH$_2$), 6.5–7.2 (m, 4H, aromatic H)

EXAMPLE 3

In a nitrogen gas stream, a solution of 1,3,3-trimethyl-2-methyleneindoline (1.26 g, 7.28 mmol) was added to hexacarbonyl chromium (1.64 g, 7.47 mmol) in anhydrous butyl ether (3 ml) followed by addition of 4 ml of anhydrous butyl ether and 1.5 ml of anhydrous tetrahydrofuran. This solution was heated in a nitrogen gas stream at 140° C. for 28 hours under constant irradiation with a 100 W low-pressure mercury vapor lamp. After completion of the reaction, the reaction mixture was filtered through Celite when hot under a nitrogen blanket to give a yellow filtrate. The light yellow needles obtained from this yellow solution were found to be $\eta^6$-1,3,3-trimethyl-2-methyleneindoline (tricarbonyl) chromium.

Yield 1.21 g, 53%
$^1$H-NMR (400 MHz, CDCl$_3$): $\delta$ppm
1.35 (s, 3H, 3-CH$_3$), 1.51 (s, 3H, 3-CH$_3$), 2.92 (s, 3H, N-CH$_3$), 4.12 (s, 2H, 2-CH$_2$), 4.71 (t, 1H, 5-CH), 4.81 (d, 1H, 7-CH), 5.51 (t, 1H, 6-CH), 5.70 (d, 1H, 4-CH)
IR (KBr): 2971, 1942, 1865, 1847, 1633, 1551 cm$^{-1}$
MS (EI, 20 eV) m/z =309 (M$^+$)

EXAMPLE 4

In a nitrogen gas stream, $\eta^6$-1,3,3-trimethyl-2-methyleneindoline(tricarbonyl)chromium (498.8 mg, 1.61 mmol) was dissolved in anhydrous methanol (25 ml) followed by addition of a solution of 5-nitrosalicylaldehyde (270 mg, 1.60 mmol) in anhydrous methanol (3.7 ml) in small portions. The mixture was stirred at 25° C. for 141 hours to give a suspension consisting of a red solution and an orange-colored precipitate. The orange-colored precipitate was recovered, washed with methanol and dried in vacuo. The resulting yellow powder was found to be 1,3,3-trimethyl-6'-nitrospiro[(2'H)-1'-benzopyran-2"2-($\eta^6$-indoline) -indoline)-(tricarbonyl) chromium].

Yield 262.7 mg, 36%

The IR spectrum of the above yellow powder is shown in FIG. 1.

$^1$H-NMR (400 MHz, CDCl$_3$) $\delta$ppm
1.21 (s, 3H, 3-CH$_3$), 1.33 (s, 3H, 3-CH$_3$), 2.72 (s, 3H, N—CH$_3$), 4.82 (t, 1H, J=4.85 Hz, 5-CH), 4.85 (d, 1H, J=4.93 Hz, 7-CH), 5.53 (t, 1H, J= 5.17 Hz, 6-CH), 5.57 (d, 1H, J=4.96 Hz, 4-CH), 5.62 (d, 1H, J=10.28 Hz, 3,-CH), 6.93 (d, 1H, J=10.28 Hz, 4,-CH), 7.20 (d, 1H, J=9.00 Hz, 8'-CH), 8.01 (d, 1H, J=2.56 Hz, 5-CH), 8.11 (dd, 1H, J=9.04 Hz, 2.64 Hz, 7'-CH)

$^{13}$C-NMR (100 MHz, CDCl$_3$) $\delta$ppm
21.3 (3-CH$_3$), 26.4 (3-CH$_3$), 28.3 (N-CH$_3$), 51.2, 70.5 (5-CH), 83.0 (7-CH), 90.5 (6-CH), 94.7 (4-CH), 103.4, 104.3, 116.5 (8,-CH), 120.0 (3'-CH), 122.6 (5'-

CH), 126.4 (7'-CH), 128.8 (4'—CH), 141.5, 158.4, 183.9, 234.2 (CR-CO)

The organochromium complex thus obtained exhibited photochromism in solvents such as benzene, methylene chloride and acetone. Thus, when such a solution of the complex was irradiated with ultraviolet light using a 500 W high-pressure mercury vapor lamp adapted to transmit ultraviolet light of the wavelength of about 350 nm, it assumed a red series color. In acetone, its maximum absorption wavelength ($\lambda_{max}$) was 564 nm in substantial agreement with that of the free spiropyran compound not ligated to the metal (see below) but its $\lambda_{max}$ in benzene or methylene chloride had been shifted spectrally downfield to 500 nm.

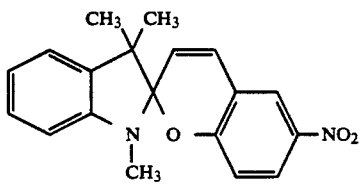

Figure 2:
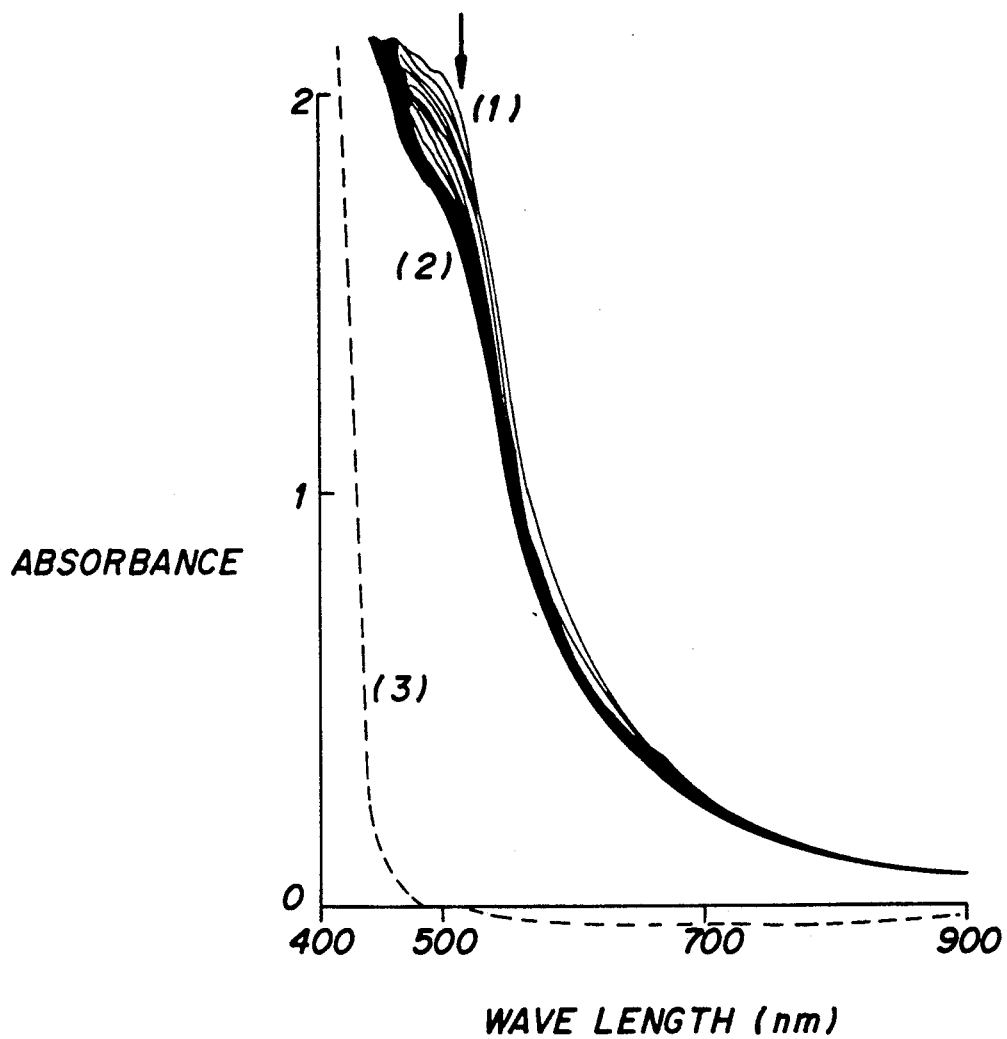
FIG. 2 is an absorption spectrum showing the fixation of the chronic response of the same complex of the invention.

These red solutions resumed the yellow color upon irradiation with light of the visible spectrum above 500 nm. Furthermore, the excited species formed by ultraviolet irradiation was very stable at room temperature and the chromic response remained stable after some initial fading. The pattern of fixation in benzene is illustrated in FIG. 2. This is in sharp contrast with the loss of color of the free spiropyran at room temperature.

EXAMPLE 5

In a nitrogen gas stream, $\eta^6$-1,3,3-trimethyl-2-methyleneindoline (tricarbonyl) chromium (309 mg, 1.00 was dissolved in anhydrous methanol (20 ml). Then, a solution of 5-nitrothiosalicylaldehyde (183 mg, 1.00 mmol) in anhydrous methanol (2 ml) was added dropwise and the mixture was stirred at room temperature for 22 hours, whereupon orange-colored crystals formed. The crystals were recovered and dried in vacuo to give (1,3,3-trimethyl-6,-nitrospiro[(2,H)-1,-benzothiopyran-2,2,-($\eta^6$-chromium]as yellow crystals. Yield 135 mg, 28.5%

The $^1$H-NMR spectrum, mass spectrum and IR spectrum of the above crystalline product were as follows.

$^1$H-NMR (400 MHz, CDCl$_3$): $\delta$ppm
1.28 (s, 3H, 3-CH$_3$), 1.45 (s, 3H, 3-CH ), 2.70 (s, 3H, N—CH$_3$), 5.20 (t, 1H, 5-CH), 5.25 (d, 1H, 7-CH), 5.59 (t, 1H, 6-CH), 5.75 (d, 1H, 4-CH), 5.77 (d, 1H, 3'-CH), 6.73 (d, 1H, 4'-CH), 7.25 (d, 1H, 8'-CH), 7.99 (d, 1H, 7'-CH), 8.07 (d, 1H, 5'-CH)

MS (EI, 20 eV) m/z=474 (M+), 428 (M+—NO$_2$), 400
(M+—NO$_2$CO$_2$), 338 (M+-Cr(CO)$_3$)

IR (KBr): 1954, 1867, 1518, 1344, 667 cm$^{-1}$

The organochromium complex thus obtained exhibited photochromism in methanol. Thus, when the complex solution was irradiated with ultraviolet light using a 500 W super-high-pressure mercury vapor lamp adapted to transmit light of about 350 nm, it assumed a red series color. The maximum absorption wavelength ($\lambda_{max}$) was 550 nm.

EXAMPLE 6

In 20 ml of benzene were dissolved 20 mg of the yellow crystals obtained in Example 4 and 100 mg of a commercial polymethyl methacrylate and the solution was cast on a glass sheet in an argon atmosphere to give a light yellow-colored photochromic film.

When this film was irradiated with ultraviolet light for 30 seconds using a 500 W super-high-pressure mercury vapor lamp fitted with a band pass filter adapted to pass light of about 350 nm, the film turned red-purple. When this chromically excited film was irradiated with visible light for 2 minutes using a 500 W super-high-pressure mercury vapor lamp fitted with a band pass filter adapted to transmit light above 500 nm, the film underwent rapid fading to show the initial light yellow color. This cycle of color change could be repeated a number of times.

I claim;
1. A transition metal-spirobenzopyran complex of the general formula

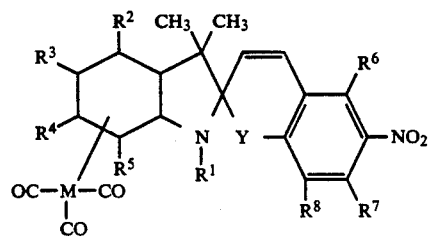

wherein $R^1$ means an alkyl group of 1 to 20 carbon atoms or an aralkyl group. $R^2$, $R^3$, $R^4$, and $R^5$ may be the same or different and each means a hydrogen atom, an alkyl group of 1 to 6 carbon atoms, an aryl group, an aralkyl group, an alkoxy group of 1 to 5 carbon atoms, a halogen atom, a cyano group or a nitro group. $R^6$ and $R^7$ may be the same or different and each means a hydrogen atom, an alkyl group of 1 to 6 carbon atoms, an aryl group, an aralkyl group, a halogen atom, a cyano group or a nitro group. $R^8$ means a hydrogen atom, an alkyl group of 1 to 6 carbon atoms, an alkoxy group or 1 to 5 carbon atoms, a chloromethyl group, a methacryloxymethyl group or a vinyl group. Y means a oxygen atom or a sulfur atom. M means a chromium atom, a molybdenum atom or a tungsten atom.

2. A process for producing the transition metal-spirobenzopyran complex of claim 1 characterized by reacting an organometallic complex of the general formula

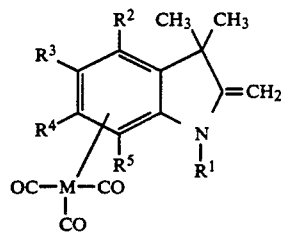

wherein $R^1$, $R^2$, $R^3$, $R^4$, $R^5$ and M are as defined above with a 5-nitro(thio)salicylaldehyde derivative of the general formula

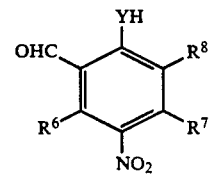

wherein $R^6$, $R^7$, $R^8$ and Y are as defined above.

3. A photochromic material comprising the transition metal-spirobenzopyran complex of claim 1.

* * * * *